(12) United States Patent
Carbone et al.

(10) Patent No.: US 8,425,837 B2
(45) Date of Patent: Apr. 23, 2013

(54) DEVICE AND METHOD FOR GAS STERILIZATION

(75) Inventors: Phil Carbone, North Reading, MA (US); Karen Benedek, Winchester, MA (US); Michael O. Ruffo, Medford, MA (US); Wade Luongo, Saugus, MA (US)

(73) Assignee: Noxilizer, Inc., Baltimore, MD (US)

( * ) Notice: Subject to any disclaimer, the term of this patent is extended or adjusted under 35 U.S.C. 154(b) by 369 days.

(21) Appl. No.: 12/710,053

(22) Filed: Feb. 22, 2010

(65) Prior Publication Data

US 2011/0085938 A1 Apr. 14, 2011

Related U.S. Application Data

(60) Provisional application No. 61/154,625, filed on Feb. 23, 2009.

(51) Int. Cl.
*A61L 2/20* (2006.01)
(52) U.S. Cl.
USPC .............................................. 422/28; 422/33
(58) Field of Classification Search ............. 422/28, 422/33
See application file for complete search history.

(56) References Cited

U.S. PATENT DOCUMENTS

| | | |
|---|---|---|
| 5,212,204 A | 5/1993 | Keefer et al. |
| 5,236,609 A | 8/1993 | Smith |
| 5,519,020 A | 5/1996 | Smith et al. |
| 5,632,981 A | 5/1997 | Saavedra et al. |
| 5,633,424 A | 5/1997 | Graves |
| 5,650,442 A | 7/1997 | Mitchell et al. |
| 5,665,077 A | 9/1997 | Rosen et al. |
| 5,683,668 A | 11/1997 | Hrabie et al. |
| 5,691,423 A | 11/1997 | Smith et al. |
| 5,698,738 A | 12/1997 | Garfield et al. |
| 5,718,892 A | 2/1998 | Keefer et al. |
| 5,785,934 A | 7/1998 | Jacobs et al. |
| 5,814,666 A | 9/1998 | Green |
| 5,840,759 A | 11/1998 | Mitchell et al. |
| 5,910,316 A | 6/1999 | Keefer et al. |

(Continued)

FOREIGN PATENT DOCUMENTS

| | | |
|---|---|---|
| CA | 2208754 C | 12/2007 |
| CA | 2582887 | 12/2007 |

(Continued)

OTHER PUBLICATIONS

International Preliminary Report on Patentability mailed Sep. 1, 2011, for PCT/US2010/024925.

(Continued)

*Primary Examiner* — Sean E Conley
(74) *Attorney, Agent, or Firm* — Pillsbury Winthrop Shaw Pittman, LLP (57) ABSTRACT

A system for gas sterilization includes a sterilization chamber, a source of sterilant gas, and a sterilant gas remediation mechanism. Embodiments relate to systems and methods for delivering humidified air to a sterilization chamber, systems and methods for removing gaseous $NO_2$ from an exhaust gas stream of a sterilization chamber, systems and methods for removing and replacing a source of sterilant gas, an exhaust gas scrubber and/or supplies for a humidification system. Some embodiments relate to hardware and software for user interface in a sterilizing device and hardware and software for control of a sterilization cycle. Some embodiments relate to chamber, chassis and door configurations of a sterilizer.

9 Claims, 8 Drawing Sheets

U.S. PATENT DOCUMENTS

| | | |
|---|---|---|
| 5,939,033 A | 8/1999 | Kendall et al. |
| 5,962,520 A | 10/1999 | Smith et al. |
| 6,103,769 A | 8/2000 | Kelm |
| 6,119,480 A | 9/2000 | Germain |
| 6,200,558 B1 | 3/2001 | Saavedra et al. |
| 6,218,016 B1 | 4/2001 | Tedeschi et al. |
| 6,232,336 B1 | 5/2001 | Hrabie et al. |
| 6,270,779 B1 | 8/2001 | Fitzhugh et al. |
| 6,290,981 B1 | 9/2001 | Keefer et al. |
| 6,379,660 B1 | 4/2002 | Saavedra et al. |
| 6,524,624 B1 | 2/2003 | Morelli et al. |
| 6,673,338 B1 | 1/2004 | Arnold |
| 7,045,096 B2 | 5/2006 | D'Ottone |
| 7,122,529 B2 | 10/2006 | Ruane et al. |
| 7,288,664 B2 | 10/2007 | Kleiner |
| 8,017,074 B2 * | 9/2011 | Arnold et al. .......... 422/33 |
| 2001/0000039 A1 | 3/2001 | Toone |
| 2001/0041184 A1 | 11/2001 | Fitzhugh |
| 2002/0009604 A1 | 1/2002 | Zamora |
| 2002/0082566 A1 | 6/2002 | Stenzler |
| 2002/0098979 A1 | 7/2002 | Cutler |
| 2002/0136750 A1 | 9/2002 | Benjamin |
| 2003/0012804 A1 | 1/2003 | Cutler |
| 2003/0021825 A1 | 1/2003 | Pathak |
| 2003/0196966 A1 | 10/2003 | Hughes |
| 2003/0228564 A1 | 12/2003 | Edrich |
| 2004/0022673 A1 | 2/2004 | Protic |
| 2004/0028596 A1 | 2/2004 | Kleiner |
| 2004/0087963 A1 | 5/2004 | Ossipov |
| 2004/0121940 A1 | 6/2004 | De Groot |
| 2004/0220265 A1 | 11/2004 | Martin |
| 2005/0113450 A1 | 5/2005 | Thorarensen |
| 2005/0158206 A1 | 7/2005 | Moisan |
| 2005/0186310 A1 | 8/2005 | Paganessi |
| 2005/0203069 A1 | 9/2005 | Arnold |
| 2005/0279713 A1 | 12/2005 | Osborn |
| 2006/0020166 A1 | 1/2006 | Berall |
| 2006/0068031 A1 | 3/2006 | Miller |
| 2006/0088469 A1 | 4/2006 | Perez-Ramirez |
| 2006/0095120 A1 | 5/2006 | Herrmann |
| 2006/0165858 A1 | 7/2006 | Yuan |
| 2006/0251824 A1 | 11/2006 | Boulais |
| 2006/0275340 A1 | 12/2006 | Udipi |
| 2007/0003589 A1 | 1/2007 | Astafieva et al. |
| 2007/0014686 A1 | 1/2007 | Arnold et al. |
| 2007/0087025 A1 | 4/2007 | Fitzhugh |
| 2007/0116785 A1 | 5/2007 | Miller |
| 2007/0196428 A1 | 8/2007 | Glauser |
| 2007/0224239 A1 | 9/2007 | Behan |
| 2007/0225785 A1 | 9/2007 | Park |
| 2007/0264225 A1 | 11/2007 | Cheng |
| 2007/0275100 A1 | 11/2007 | Miller |
| 2007/0286882 A1 | 12/2007 | Tang |
| 2008/0029093 A1 | 2/2008 | Stenzler |
| 2008/0097575 A1 | 4/2008 | Cottone |
| 2008/0175881 A1 | 7/2008 | Ippoliti |
| 2008/0183276 A1 | 7/2008 | Melder |
| 2008/0213403 A1 | 9/2008 | Martin |
| 2008/0220046 A1 | 9/2008 | Cheng |
| 2008/0220048 A1 | 9/2008 | Chen |
| 2008/0233212 A9 | 9/2008 | Miller |
| 2008/0268524 A1 | 10/2008 | Cachon |
| 2008/0286321 A1 | 11/2008 | Reneker |
| 2008/0314289 A1 | 12/2008 | Pham |
| 2008/0317626 A1 | 12/2008 | Arnold |
| 2008/0317813 A1 | 12/2008 | Craig |
| 2008/0317939 A1 | 12/2008 | Dehnad |
| 2009/0022769 A1 | 1/2009 | Chen |
| 2009/0035350 A1 | 2/2009 | Stankus |
| 2009/0041845 A1 | 2/2009 | Kleiner |

FOREIGN PATENT DOCUMENTS

| | | |
|---|---|---|
| CN | 1505930 A | 6/2004 |
| EP | 0475505 | 3/1992 |
| EP | 0410118 B1 | 4/1994 |
| EP | 0674845 A1 | 10/1995 |
| EP | 0818212 A3 | 7/1998 |
| EP | 1704877 A1 | 9/2006 |
| EP | 1722223 A1 | 11/2006 |
| EP | 1370298 B1 | 10/2008 |
| GB | 983073 A | 2/1965 |
| GB | 2384185 A | 11/2003 |
| GB | 2393393 | 3/2004 |
| JP | 63126598 A2 | 5/1988 |
| JP | 2-134322 A2 | 5/1990 |
| JP | 2-208204 A2 | 8/1990 |
| JP | 3-77698 A2 | 4/1991 |
| JP | 3-282101 A2 | 12/1991 |
| JP | 4-66510 A2 | 3/1992 |
| JP | 4-118099 A2 | 4/1992 |
| JP | 2001198419 A2 | 7/2001 |
| KR | 2000-0030368 A | 6/2000 |
| KR | 2003-0067338 A | 8/2003 |
| KR | 10-2004-038041 A | 5/2004 |
| RU | 2260959 C2 | 9/2005 |
| WO | WO9116083 | 10/1991 |
| WO | WO9116083 A1 | 10/1991 |
| WO | WO96/09210 | 3/1996 |
| WO | WO96/31217 | 10/1996 |
| WO | WO9631217 A1 | 10/1996 |
| WO | WO9805689 A1 | 2/1998 |
| WO | WO9808689 A1 | 2/1998 |
| WO | WO9956892 A1 | 11/1999 |
| WO | WO96/67210 | 12/1999 |
| WO | WO9967210 A1 | 12/1999 |
| WO | WO0186289 A1 | 11/2001 |
| WO | WO0243786 A2 | 6/2002 |
| WO | WO03017996 A1 | 3/2003 |
| WO | WO03026717 A1 | 4/2003 |
| WO | WO03/047777 | 6/2003 |
| WO | WO03/051407 | 6/2003 |
| WO | WO03/063914 A2 | 8/2003 |
| WO | WO03/63914 A2 | 8/2003 |
| WO | WO03066109 A1 | 8/2003 |
| WO | WO03/080132 | 10/2003 |
| WO | WO2004011039 A2 | 2/2004 |
| WO | WO2004018368 A1 | 3/2004 |
| WO | WO2004067448 A1 | 8/2004 |
| WO | WO2005029036 A2 | 3/2005 |
| WO | WO2005/044315 A2 | 5/2005 |
| WO | WO 2005/067986 | 7/2005 |
| WO | WO2005067986 A1 | 7/2005 |
| WO | WO2005082174 A1 | 9/2005 |
| WO | WO2005105065 A2 | 11/2005 |
| WO | WO2006053004 A2 | 5/2006 |
| WO | WO2006100156 A2 | 9/2006 |
| WO | WO2006128121 A2 | 11/2006 |
| WO | WO2007005910 A2 | 1/2007 |
| WO | WO2007008618 A2 | 1/2007 |
| WO | WO2007015739 A2 | 2/2007 |
| WO | WO2007105739 A2 | 2/2007 |
| WO | WO2007036775 A1 | 4/2007 |
| WO | WO2007067477 A1 | 6/2007 |
| WO | WO2007092043 A2 | 8/2007 |
| WO | WO2007146231 A2 | 12/2007 |
| WO | WO2008005313 A2 | 1/2008 |
| WO | WO2008018820 A1 | 2/2008 |
| WO | WO2008051881 A2 | 5/2008 |
| WO | WO2008055718 A3 | 5/2008 |
| WO | WO2008095841 A2 | 8/2008 |
| WO | WO2008112391 A2 | 9/2008 |
| WO | WO2008127889 A2 | 10/2008 |
| WO | WO2008148013 A1 | 12/2008 |
| WO | WO2009017855 A2 | 2/2009 |

OTHER PUBLICATIONS

European Office Action issued in corresponding European Application No. 10705518.8, dated Nov. 21, 2011, 4 pages.

Ellies et al., "Crystallographic structure and surface morphology of sintered carbonated apatites," *J. Biomed Mater. Res.*, 1998, 22(6):541-53.

EP 05704995.9 Supplementary European Search Report Completed on Apr. 16, 2009.

Enomoto et al., "Inactivation of food microorganisms by high-pressure carbon dioxide treatment with or without explosive decompression," *Biosci. Biotech. Biochem.*, 1997, 61(7):1133-7.

Hetrick, et al., "Reducing implant-related infections: active release strategies," *Chem. Soc.Rev.*, 2006, 35(9):780-9.

Populaire, et al., "An armoured endotracheal tube obstruction in a child," *Can. J. Anaesth.*, 1989, (3 pt 1) 331-2.

Sharpless et al., "UV photolysis of nitrate: effects of natural organic matter an dissolved in organic carbon and implications for UV water disinfection," *Environ Sci. Technol.*, 2001, 35(14):2949-55.

Sharpless et al., "Impact of hydrogen peroxide on nitrite formation during UV disinfections," *Water Res.*, 2003, 37(19):4730-6.

Smith et al., "Dental implant materials. I. Some effect of preparative procedures on surface topography," *J. Biomed Mater Res.*, 1991, 9:1045-68.

Young et al., "Microwave sterilization of nitrous oxide nasal hoods contaminated with virus," *Oral Surg. Oral Med Oral Pathol.* 1985, 60(6): 58-585.

* cited by examiner

FIG. 9

US 8,425,837 B2

DEVICE AND METHOD FOR GAS STERILIZATION

This application claims the benefit of U.S. Provisional Application 61/154,625, filed Feb. 23, 2009, the contents of which are incorporated by reference herein in their entirety.

FIELD OF THE INVENTION

The invention relates generally to systems and methods for sterilization using oxides of nitrogen. More particularly, it relates to systems and methods for delivering gaseous $NO_2$ to a sterilization chamber containing one or more objects to be sterilized. Embodiments relate to systems and methods for delivering humidified air to a sterilization chamber, systems and methods for removing gaseous $NO_2$ from an exhaust gas stream of a sterilization chamber, systems and methods for removing and replacing a source of sterilant gas, an exhaust gas scrubber and/or supplies for a humidification system. Embodiments relate to hardware and software for user interface in a sterilizing device and hardware and software for control of a sterilization cycle. Embodiments relate to chamber, chassis and door configurations of a sterilizer, including ornamental aspects thereof.

DESCRIPTION OF THE RELATED ART

Sterilization methods are known that rely on chemicals, pressure and temperature to eliminate biological contaminants such as bacteria, spores and fungi from a variety of substrates including medical devices, medical compounds and others. Alternately, radiation-based treatments may be used, avoiding some types of damage to the object to be sterilized that can result from heat and pressure. In another approach, ethylene oxide, ozone and peroxide gas sterilization techniques have been used.

In particular, pharmaceutical formulations may have a great deal of sensitivity to damage from heat and pressure, leaving radiation as an option for sterilization of these compounds. However, radiation having appropriate energies and penetration characteristics for sterilization may also have the effect of damaging the pharmaceutical, substrate and/or delivery substrate itself. Likewise, shape memory materials are susceptible to heat related phase transitions that may be addressed using methods in accordance with embodiments of the present invention.

SUMMARY OF THE INVENTION

One aspect of the invention relates to a device for delivering gaseous $NO_2$ to a sterilization chamber containing one or more objects to be sterilized. The device includes a sterilization chamber, a source of sterilant gas, and a sterilant gas remediation mechanism.

Aspects of embodiments relate to systems and methods for delivering humidified air to a sterilization chamber, systems and methods for removing gaseous $NO_2$ from an exhaust gas stream of a sterilization chamber, systems and methods for removing and replacing a source of sterilant gas, an exhaust gas scrubber and/or supplies for a humidification system.

Aspects of embodiments relate to hardware and software for user interface in a sterilizing device and hardware and software for control of a sterilization cycle.

Aspects of embodiments relate to chamber, chassis and door configurations of a sterilizer, including ornamental aspects thereof.

Another aspect of the invention relates to a method for delivering gaseous $NO_2$ to a sterilization chamber containing one or more objects to be sterilized.

Yet another aspect of the invention relates to a system configured to control the foregoing device or, method including controlling one or more of sterilant gas concentration, humidity, temperature, gas circulation, total or partial gas pressure and/or duration of exposure of the object or objects to be sterilized.

Aspects of embodiments of the invention relate to machine executable code embodied on a machine readable medium which, when executed, performs methods as described herein.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

In view of the issues raised with heat and radiation sterilization approaches, the inventors have determined that gas sterilization techniques based on oxides of nitrogen may provide good sterilization while mitigating damage to the sterilized substrate. In particular, the inventors have shown that nitrogen dioxide ($NO_2$) is an effective sterilization agent for a variety of biological targets.

In an embodiment, a low concentration (<21 mg/L) of nitrogen dioxide gas in the presence of air and water vapor is delivered to a sterilization chamber. In particular embodiments, concentrations of between about 5 and 15 mg/L, and preferably between about 8 and 11 mg/L are used. Lower concentrations than 5 mg/L may be used, but as concentration is reduced, dwell time should be extended. As described in greater detail below, the process may be performed at or near room temperature and entails evacuating air from the chamber, introducing the sterilant gas, and adding humidified air to a selected pressure. Depending on the physical characteristics and/or packaging of the item to be sterilized, the sequence of vacuum→sterilant injection→humid air injection, may be repeated several times or the sequence changed. Furthermore, additional sequence steps of dry air injection and dwell may be included in one or all iterations of the sterilizing sequence. At the ordinary operating temperatures and pressures of the process, the $NO_2$ remains in the gas phase and acts as an ideal gas. The cycle may include a check for water or humidity levels, and should the levels be above a threshold, a drying sequence may be engaged. Drying may include heating of the chamber, evacuating the chamber to pressures below the vapor pressure of water at the temperature of the chamber, and/or passing dry gas such as dry air or a dry inert gas through the chamber.

Figure 1A:
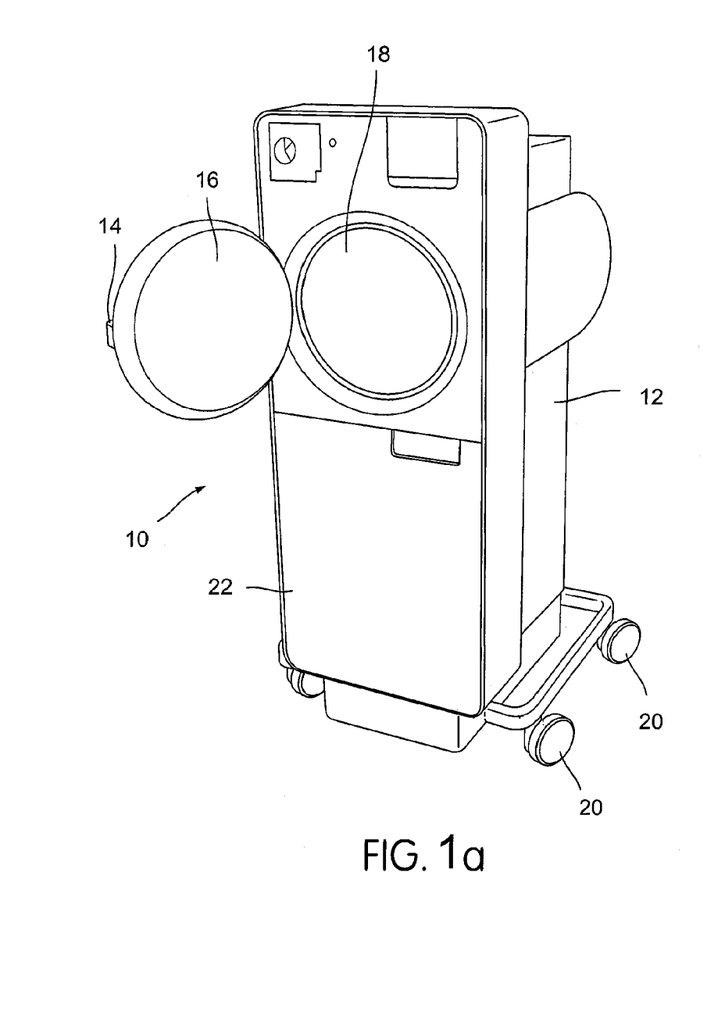
FIGS. 1a and 1b are perspective views of a system for sterilization in accordance with an embodiment of the present invention.
Figure 1B:
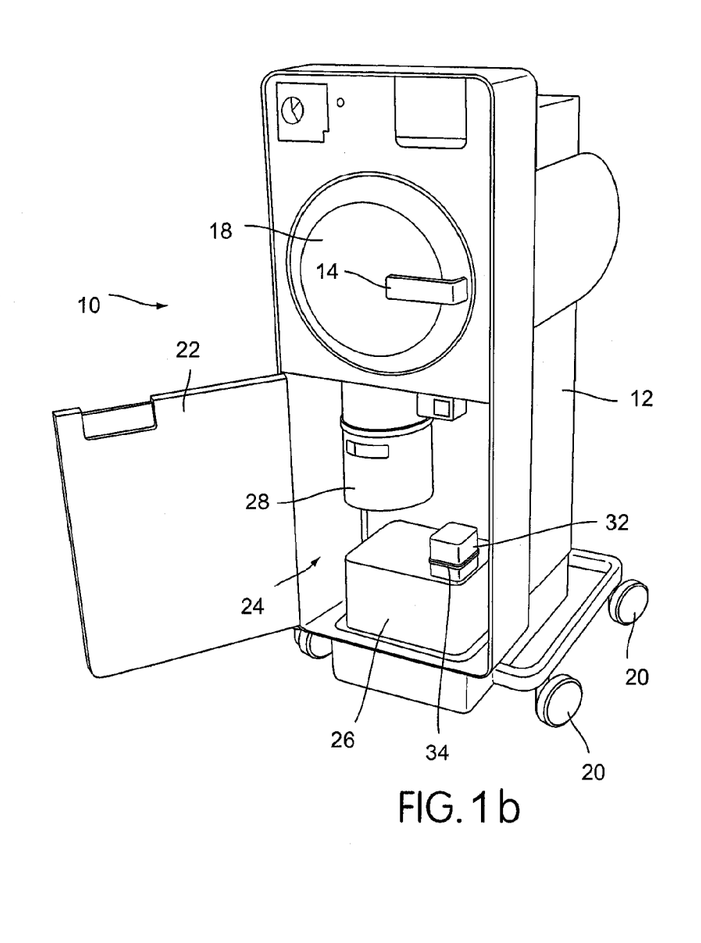

An embodiment of a sterilizer that uses $NO_2$ sterilizing gas is illustrated generally in FIGS. 1a and 1b. The sterilizer 10 includes a housing 12.

In an embodiment, the housing 12 is sized such that a handle 14 for a door 16 for the sterilizing chamber 18 is at a height suited to use by an average standing user, for example, about 42". The overall height of such a system may be about 5 feet and the width, approximately 20". As shown, the housing 12 may optionally be supported on a set of wheels 20, to allow for easy portability of the sterilizer 10.

A second door 22 is located in a lower portion of the housing 12 and allows access to serviceable portions of the sterilizer 10. In particular, consumables may be stored in the service area 24. In the embodiment shown, a sterilant gas module 26 and a scrubber 28 are located in the service area, along with a reservoir 30 for storing water to be used by a humidification system, as described below. The sterilant gas module includes a door 32 having a hinge 34 allowing it to be opened for access to replace a sterilant gas source (not shown), as described in greater detail below.

In an embodiment, the housing 12 may include an additional door (not shown) for accessing the sterilizing chamber 18, allowing for pass-through operation of the sterilizer 10. As an example, such a pass-through device may be mounted into a wall opening between a clean room or a sterile area and an area having less or no control over air quality, sterility or particle load. Such a device may find application, for example, in a medical device manufacturing plant, in a pharmaceutical plant, in product flow in a hospital sterile processing department, or a controlled sterile laboratory.

Figure 2:
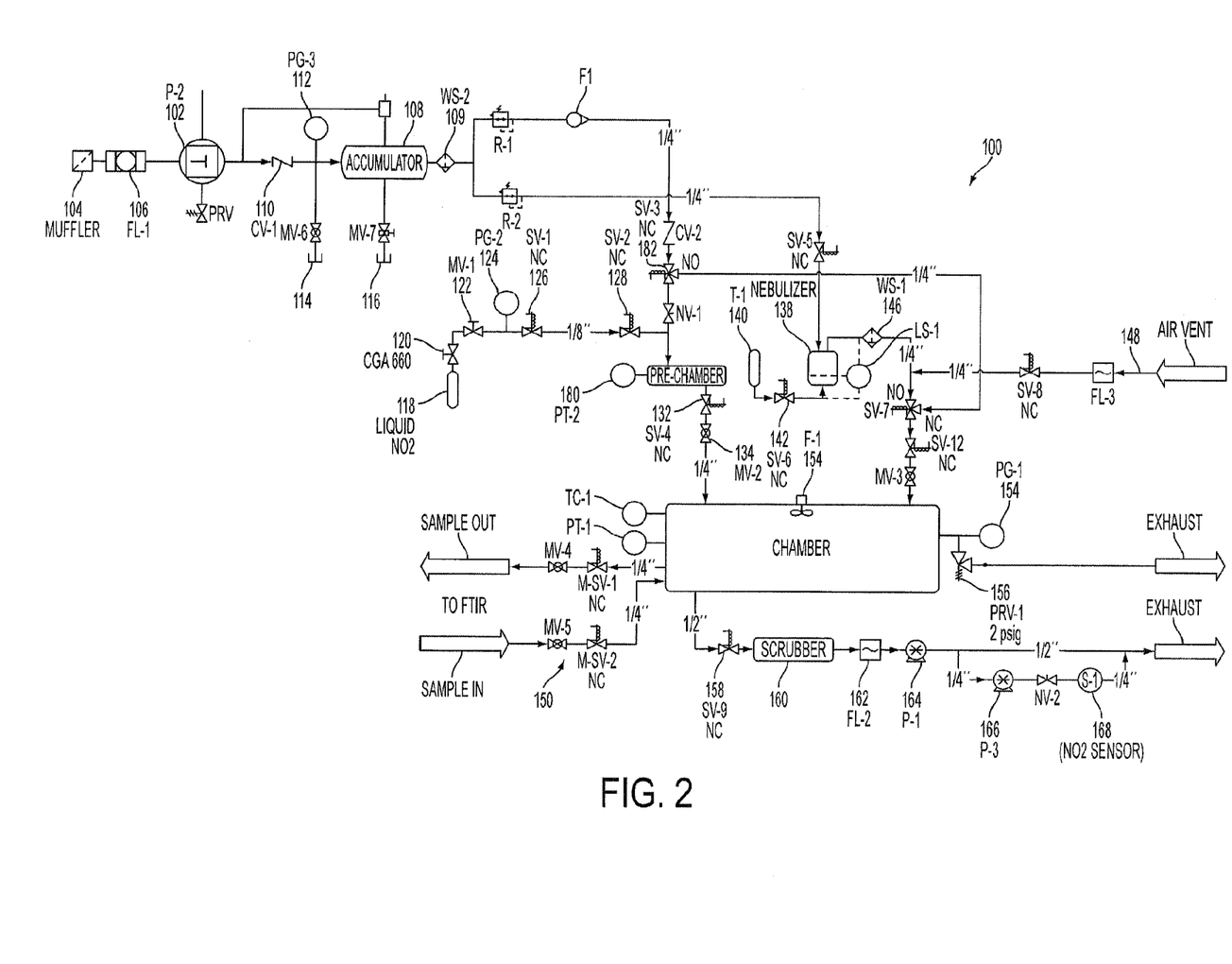
FIG. 2 is a schematic diagram showing functional interconnections for a system for sterilization in accordance with an embodiment of the present invention.

FIG. 2. is a schematic process and instrumentation diagram of an embodiment of a sterilizer 100 in accordance with the present invention. Note that while specific diameters are provided for certain of the flow paths, these should not be taken as limiting in any way, but are subject to variation in accordance with specific applications. A first portion of the sterilizer 100 is a source of air to be added to the nitrogen dioxide gas in the chamber. A compressor 102 compresses air from the ambient environment. Prior to compression, the ambient air passes through a muffler 104 and a filter 106. The filter 106 reduces dust and other particulate impurities that are generally undesirable both for the compressor and the downstream use of the compressed air. Furthermore, the filter 106 may advantageously be designed to remove microbes from the air stream such that the air delivered to the sterilizer, and in particular to the humidification system, is substantially pathogen free. As will be appreciated, other sources of air may be substituted. For example, air may be provided by air tanks or a fixed air supply system that provides pressurized air to the room in which the sterilizer is housed.

As shown, the air is supplied from the compressor 102 to an accumulator 108 via a control valve 110. In the illustrated embodiment, pressure in the accumulator 108 is controlled via a feedback loop to the control valve 110 using a pressure gage 112. Manual valves 114, 116 are optionally provided to allow pressure relief and water drain from the accumulator 108 respectively. A water separator 109 may be included to ensure that liquid water does not enter the air stream on the downstream side of the accumulator.

Nitrogen dioxide is provided to the system from a liquid supply tank 118. A manual valve 120 and a valve 122 control flow from the supply tank 118. A pressure gage 124 allows monitoring of pressure in the lines and a pair of solenoid valves 126, 128 control flow into a pre-chamber 130. Another pair of valves 132, 134 control flow from the pre-chamber 130 to the sterilization chamber 136. Though illustrated in FIG. 2 as a simple pipe connection, the flow into the chamber 136 may alternately be provided using a manifold, allowing for improved distribution of the sterilant gas within the chamber. While the illustrated embodiment involves only transport of gaseous $NO_2$, it is envisioned that liquid $NO_2$ could flow to the pre-chamber prior to vaporization. More detail of the operation of the $NO_2$ delivery sub-system is discussed below.

A sub-system for providing humidity to the sterilization chamber 136 begins with a Collison nebulizer 138 that produces aerosolized water in air to be provided to the sterilization chamber 136. The air for this process is provided by the accumulator 108, similarly to the air used in the pre-chamber 130. Water for humidification is stored in the reservoir 140, and a solenoid valve 142 controls water flow from the reservoir 140 into the nebulizer 138. A level sensor 144 monitors the water level in the nebulizer 138 and controls the opening of the solenoid valve 142. As the pressurized air enters the nebulizer, it generates a sonic velocity air jet in water held in the nebulizer. The air jet aspirates the water, forming small droplets which then vaporize. A water separator 146 prevents liquid water from entering the sterilization chamber 136 while allowing the humid air to pass through. An air vent 148 provides a vent pathway from the nebulizer allowing the water to flow from the reservoir 140 to the nebulizer 138. Suitable valves control the entry of the humidified air to the sterilization chamber 136.

As illustrated, the sterilization chamber 136 includes access via a set of valves 150 so that samples of the chamber atmosphere may be taken and analyzed. Analysis may be, for example, by an FTIR, UV spectrophotometric, or other appropriate spectrometry system, not shown. Access for analysis has particular relevance to a test platform, and may be unnecessary in practice when the sterilizer is used in a production environment.

The sterilization chamber 136 may include a fan 152 that helps to circulate gases in the chamber. Circulation helps to ensure both that the sterilant gas is well mixed with the humidified air, and that objects to be sterilized are well exposed to the sterilant gas.

A pressure gage 154 and pressure relief valve 156 may be provided to control pressures in the sterilization chamber 136. As will be appreciated, in the case that exhaust from the pressure relief pathway contains nitrogen dioxide, it should be controlled or processed to avoid contamination of the work area.

The primary exhaust pathway proceeds through a solenoid valve 158 to a scrubber 160, designed to eliminate and/or capture nitrogen dioxide before the exhaust reaches the environment. A filter 162 removes particulates from the exhaust. Pump 164 pushes scrubbed exhaust out of the system. Another pump 166 provides a flow through an $NO_2$ sensor 168 for monitoring $NO_2$ content of the exhaust gases. Should the $NO_2$ levels exceed a selected threshold, solenoid valve 158 can be closed to ensure that $NO_2$ is not released into the environment. As will be appreciated, the order between the pump 166 and the sensor 168 may be reversed, allowing for sensing prior to the control valve rather than after.

Figure 3:
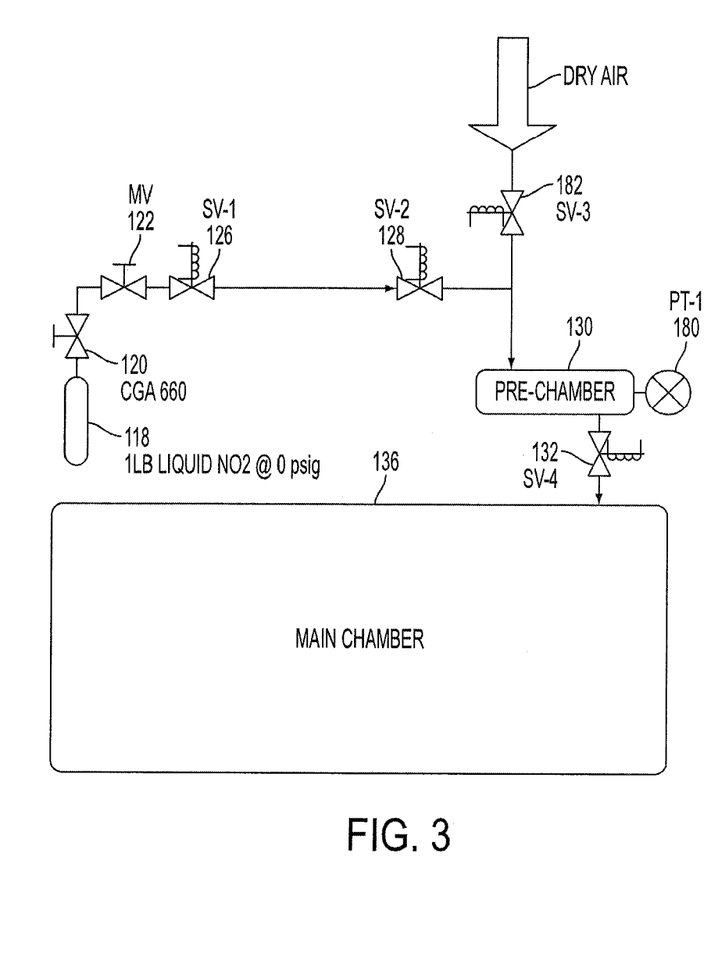
FIG. 3 is a schematic diagram showing functional interconnections for a sterilant gas delivery subsystem in accordance with an embodiment of the present invention.

FIG. 3 illustrates an embodiment of a sterilant delivery system similar in configuration to the sterilant delivery subsystem of FIG. 2. A tank 118 containing liquid $NO_2$ acts as the source of sterilant gas. A manual valve 120 provides a flow of gas from the tank 118. A manual valve 122 provides a secondary control over flow from the tank. A pair of solenoid valves 126, 128 are actuatable to allow flow from the valve to the sterilizing system. As illustrated, there are four separate valves that ultimately control flow from the tank 118. As will be appreciated, other valve arrangements are possible, and redundancy may be reduced or eliminated, as desired.

During use, sterilant gas is allowed to flow from the final solenoid valve 128 into a pre-chamber 130, where it expands and the dosage may be measured. As shown, the pre-chamber 130 includes a pressure transducer 180 that allows measurement of a total pressure which may be translated into dosage, given appropriate knowledge of the size of the chamber and optionally, temperature data derived from a temperature sensor, not shown. A solenoid valve 132 controls flow into the sterilizing chamber 136. An additional solenoid valve 182 controls flow of dry air into the pre-chamber.

In one method of operating the illustrated embodiment, the chamber 136 and pre-chamber 130 are initially at low pressure, for example, they may be evacuated using appropriate vacuum pumps (for example, the pump 164 in the exhaust pathway illustrated in FIG. 2). In an embodiment, an evacuation cycle is repeated prior to injection of the sterilant gas. As an example, the chambers may be evacuated, re-filled with air, and then evacuated again prior to initiating the sterilant gas sequence.

In order to begin delivery of sterilant gas, valve 128 is closed and 132 is opened, while valve 182 is held closed, equalizing the pressure in the chamber 136 and pre-chamber 130 at a low pressure. Valve 132 is closed, isolating the pre-chamber 130 from the sterilizing chamber 136. Valves 126 and 128 are then opened (valve 122 and manual valve 120 having been already opened) and gas that has boiled off of the liquid $NO_2$ supply is allowed to enter the pre-chamber 130. The pressure transducer 180 may be used in a feedback arrangement to control solenoid valve 126 such that a selected total amount of $NO_2$ is collected in the pre-chamber 130.

As will be appreciated, if volume of the pre-chamber 130, pressure and temperature are known, for example via measurements using the pressure transducer 180 and a temperature gage (not shown), the total amount of $NO_2$ in the pre-chamber 130 may be calculated. By way of example, an operating pressure of 10-20 inHg may be generated in order to provide an approximately 0.5 gram dose of sterilant to a sterilization chamber 136 having a volume of about 60 liters. In this approach, a concentration of about 10 mg/L of sterilant gas is produced in the sterilization chamber 136.

For a particular device in a particular setting, because the volume of the chamber does not change, and temperatures will not fluctuate significantly, the process of preparing a dose may be controlled with pressure measurements alone, without any calculating steps. Thus, when a pressure threshold is reached in the pre-chamber, the appropriate dose is present and the connection between the source and the pre-chamber may be closed. In an embodiment, there may be a table of pressure set points, for example, stored in memory accessible to the controller, that correspond to desired dosages. In another embodiment, there may be a curve stored in memory accessible to the controller that associates dose with pressure set points. In either approach, the measured pressure during a filling operation may be compared to the set point pressure derived from either the table or the curve. Where temperature is more variable, adjustments may be made based on a measured temperature, and those adjustments may be calculated, or derived from a table or curve stored in a memory.

As will also be appreciated, it is possible for other species of nitrogen oxides to form in the pre-chamber. As a result, it may be useful to account for partial pressures of various species in calculating the total deliverable dose of sterilant gas. The inventors have determined that the primary species present at the pressures observed is the dimer $N_2O_4$. Because partial pressures of oxides of nitrogen in the (generally much larger) sterilization chamber 136 are substantially lower than in the pre-chamber 130, the dimerization of $NO_2$ is less prevalent and partial pressures remain at a low level and are not generally important. That is, the total mass of the $NO_2$ and $N_2O_4$ is generally available as $NO_2$ in the sterilization chamber 136.

After the pre-chamber 130 is pressurized, the valves 126 and 128 are closed, isolating the pre-chamber 130 from the gas source. Valve 132 is opened, allowing the gas from the pre-chamber 130 to pass into the sterilizing chamber 136. Valve 182 is opened to allow dry air to enter into the sterilizing chamber 136, and to push any remaining sterilant gas out of the pre-chamber 130 and into the sterilizing chamber 136. Finally, valves 182 and 132 are closed, isolating the sterilizing chamber from the other portions of the system.

In an embodiment, the additional chamber, which may be the pre-chamber, or an additional chamber, is used to circulate the sterilizing gas into and out of the sterilizing chamber. For example, a pre-chamber or co-chamber of sufficient size may be used for recycling the sterilizing atmosphere. In this case, the sterilization cycle may be initiated in the manner described with respect to the other embodiments. The pre-chamber or co-chamber can be opened to the sterilizing chamber, via a circuit that may include a pump for driving the gas from the sterilizing chamber to the alternative chamber volume. Then, the gas can be re-introduced to the sterilizing chamber. This re-introduction may occur one time, more than one time, or the gases may be continuously transferred from one chamber to the other. Each cycle may be the same as other cycles, or each cycle may have different parameters including, for example, longer or shorter dwell times, greater or lesser concentrations of sterilant gas, and higher or lower pressures. The inventors have determined that repeated exposure cycles may be more effective for sterilization than a longer dwell, single exposure cycle. The removal and re-introduction of the sterilant gas may achieve the same ends as would entirely cycling out the gas and cycling in new sterilant gas during repeated exposure cycles.

The concentration of sterilant or the humidity of the gases being transferred between the two chambers may be adjusted to maintain lethal exposure conditions. In particular, upon depressurization and re-pressurization of the gas in the chamber, it would be expected that humidity changes would occur.

As will be appreciated, other configurations and methods may be used to provide the sterilant gas to the sterilizing chamber 136. For example, a gas source may be used in place of the liquid source. The source may be a single use source, or multiple use source as shown. Other valving arrangements and control sequences may replace those described herein. Liquid or solid source material may be provided directly to the sterilizing chamber 136, without first being converted to a gas. As an example, a material that is known to produce NO (which may be converted to $NO_2$ in use) is described in U.S. patent application Ser. No. 11/052,745, filed Sep. 15, 2005, and herein incorporated by reference in its entirety. Likewise, gas may be delivered at varying concentrations to the chamber. That is, while the described method provides a high concentration sterilant gas to the chamber, there may be greater or lesser degrees of mixing with air prior to delivery.

In an embodiment, a non-reactive gas or gas mixture rather than dry air is added to dilute the sterilant gas. For example, $N_2$ gas may be used in place of air. In this approach, the $N_2$ gas may be used dry, humidified prior to adding to the sterilization chamber 136, or may alternately be humidified in the sterilization chamber 136, as with the embodiments using air.

Figure 4A:
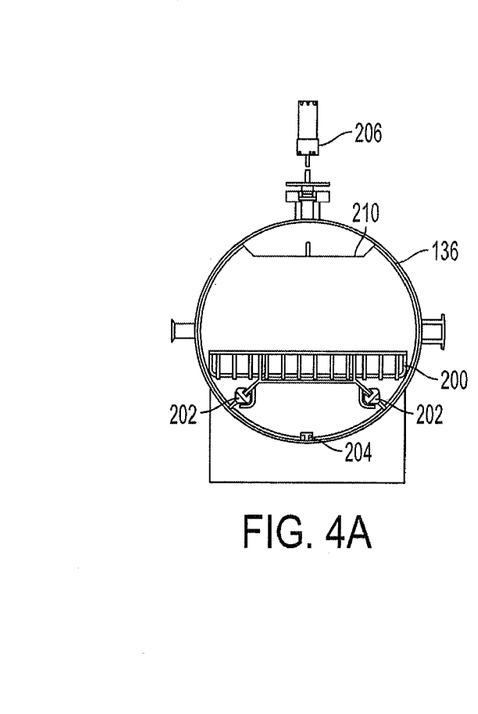
FIG. 4a is a front cutaway view of a sterilization chamber in accordance with an embodiment of the present invention.
Figure 4B:
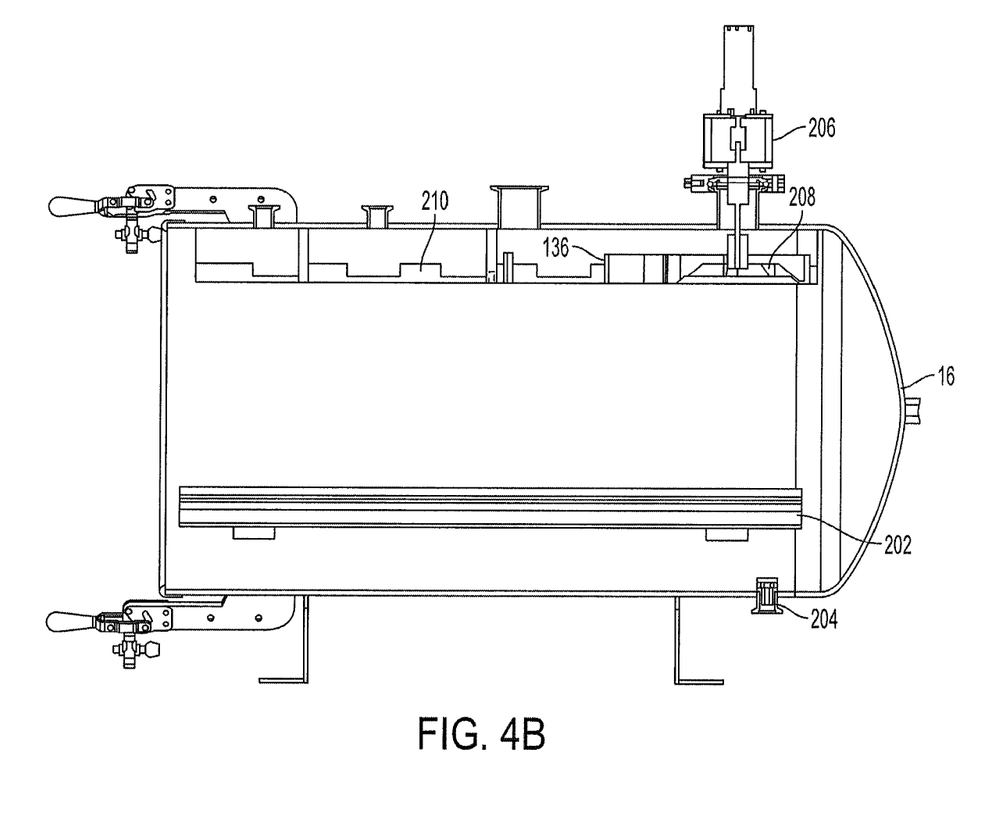
FIG. 4b is a side cutaway view of a sterilization chamber in accordance with an embodiment of the present invention.

FIGS. 4a and 4b illustrate an embodiment of a sterilization chamber 136 in greater detail. In an embodiment, the sterilization chamber 136 has a perfluoroalkoxy (PFA) coating on its interior surface. Because PFA coatings may be manufactured to be non-porous and/or hydrophobic, heterogeneous liquid formation on surfaces of the chamber may be reduced. Such reduction of liquid water formation may help to control humidity within the chamber, for example by ensuring that humidity added to the sterilant atmosphere in the chamber remains vaporized as a component of the atmosphere. Furthermore, such a smooth surface can facilitate cleaning and maintenance of a sterile environment within the chamber. As will be appreciated, other materials having similar properties may be substituted, for example, stainless steel.

As seen in FIG. 4a, the sterilization chamber 136 may include a rack 200 for holding objects during sterilization. In the embodiment as shown, the rack 200 is slidably mounted on a pair of rails 202 for ease of access. A port 204 connects to the exhaust pathway and the scrubber 160, as shown in FIG. 2.

Optionally, a motor 206 is operatively engaged with a fan 208 that may be driven to improve mixing and circulation within the sterilization chamber 160. A baffle 210 is positioned in an upper region of the chamber. The baffle may be configured and arranged to ensure that the fan does not directly blow on objects being sterilized and also to assist in creating airflows that ensure good circulation of gases through the chamber. In particular, when used with a generally cylindrical chamber, the illustrated baffle, having openings along upper sides of the chamber, will tend to create airflows circulating along outer regions of the chamber, and returning along a central region. The arrow in FIG. 4a illustrates an example of such a flow circulating through the chamber along a path originating at an edge of the baffle and continuing along the surface of the cylinder and returning up the center of the chamber.

Figure 5:
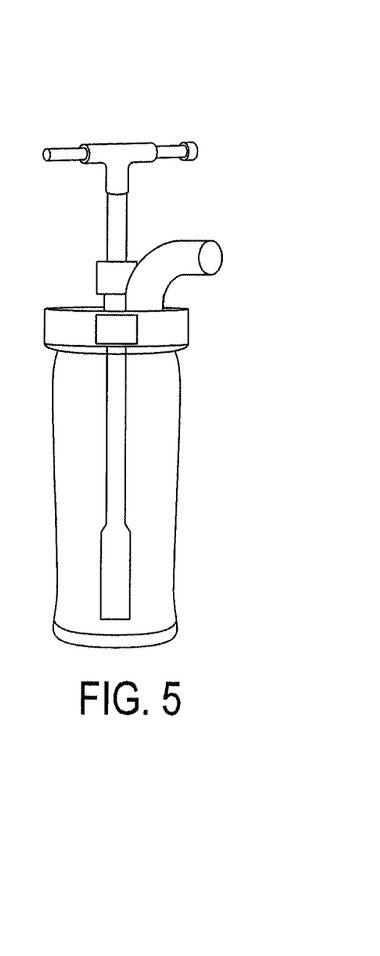
FIG. 5 is an illustration of a Collison nebulizer for use in a humidification subsystem of a sterilizer in accordance with an embodiment of the present invention.
Figure 6:
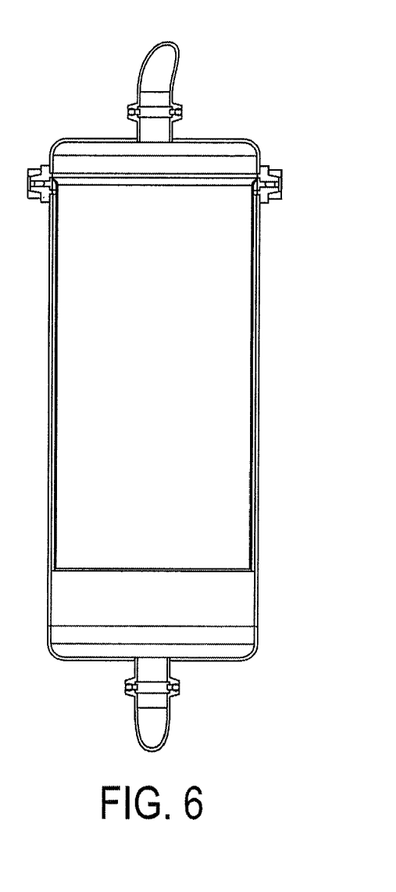
FIG. 6 is an illustration of a scrubber for removing sterilant gas from an exhaust of a sterilizer in accordance with an embodiment of the present invention.

In an embodiment, humidity is added to the sterilization chamber 136 by way of a Collison nebulizer 138 as shown in FIG. 2. FIG. 5 is an illustration of a Collison nebulizer of a type that may be suitable for use in a system in accordance with the present invention. In operation, the Collison nebulizer is attached to a source of compressed air. As illustrated in FIG. 2, this may be an alternate path from the accumulator 108. As will be appreciated, alternately a separate air source may be employed. The nebulizer may include a fill adaptor that allows it to be continuously refilled from the reservoir 30 during use.

In an alternate embodiment, water vapor may be directly added to the sterilization chamber. In another approach, the nebulizer may be replaced with a humidifier of another design, such as evaporative, steam, impeller or ultrasonic humidifiers. Finally, it is feasible to provide liquid water or water carried by a substrate (such as a moist sponge, towel or other absorptive material) directly to the sterilization chamber in order to provide humidity.

Because relative humidity is dependent in part on temperature, it may be useful to use temperature data to determine an amount of humidified air necessary to achieve a target humidity level in the chamber. In this regard, a temperature sensor, not shown, may be provided in the sterilization chamber.

As described above, the exhaust pathway includes a scrubber 160 for removing sterilant gas from the exhaust stream, prior to venting to the exterior of the system. The scrubber 160 may be, for example, embodied in a cartridge filter type of device as illustrated in FIG. 6. A cartridge of this type may be placed in-line in the exhaust pathway, such that gases pulled out of the sterilization chamber 136 via the pump 164 will pass through the cartridge.

In an embodiment, the cartridge is a cylinder having an outer sleeve area where the gas to be treated enters. Perforations in an inner sleeve allow the gas to flow through to the treating medium, thence to an outlet to the exhaust pathway.

The medium is selected to convert the reactive oxides of nitrogen into non-reactive products or otherwise neutralize any hazard associated with the sterilant gas. The scrubber material may be provided in granular form, smaller granules providing a greater surface area per unit volume of scrubbing material. In an embodiment, a sodium permanganate material has been found to be suitable for oxidation of $NO_x$ to nitrate (i.e., NO to $NO_2$ and $NO_2$ to $NO_3$). In particular, granular Purafil SP (14×28 mesh), a sodium permanganate including activated alumina has been found to be suitable. Once oxidized, the nitrate bonds with sodium to form a solid salt which is substantially non-toxic, non-corrosive, non-reactive and does not readily ignite. In an embodiment, the cartridge may include a few kilograms of sodium permanganate at a density of about 50 $lb/ft^3$ to provide up to about one month of scrubbing capacity at typical usage rates. In embodiments, the exhaust gas may be considered to be remediated when $NO_2$ levels are reduced below applicable safety standards, and particularly, when reduced below about 5 ppm and more particularly, when reduced below about 1 ppm. In embodiments where the gas is exhausted directly outdoors, a higher level of $NO_2$ may be acceptable, and levels of 10 ppm may be considered to be sufficiently remediated.

In an embodiment, the exhaust cycle may include a series of evacuations of the sterilization chamber. In this approach, the pressure in the sterilization chamber is reduced, for example, by 90%, exhausting all but 10% of the sterilant gas. Next, a charge of air or other diluent gas is added to the chamber, and the exhausting is repeated. As will be appreciated, each cycle reduces the amount of sterilant gas by 90%, so that after three cycles, only 0.1% remains in the chamber. This may be repeated as many times as necessary to render the interior of the chamber safe. For higher percentages of exhaust (e.g., 99%), fewer repetitions are needed while for lower percentages, more repetitions will be needed (e.g., 80%) to reach a selected threshold. Using this approach, the exhaust cycle can be controlled based on pressure measurements, and the interior $NO_2$ levels may be known without requiring additional $NO_2$ monitoring equipment in the chamber or at the outlet of the chamber.

In an embodiment, replacement of the liquid $NO_2$ bottle is controlled to improve safety. Interlocks may be provided to restrict removal until all supply valves are closed and a purge sequence is performed. Optionally, the exhaust pump may be held on during cylinder disconnect to ensure that any remaining sterilant gas is vented through the scrubber and exhaust pathway rather than backflowing through the input side of the system. Similar interlocking may be implemented to prevent removal/replacement of the scrubber when sterilant gas is present in the lines.

Figure 7:
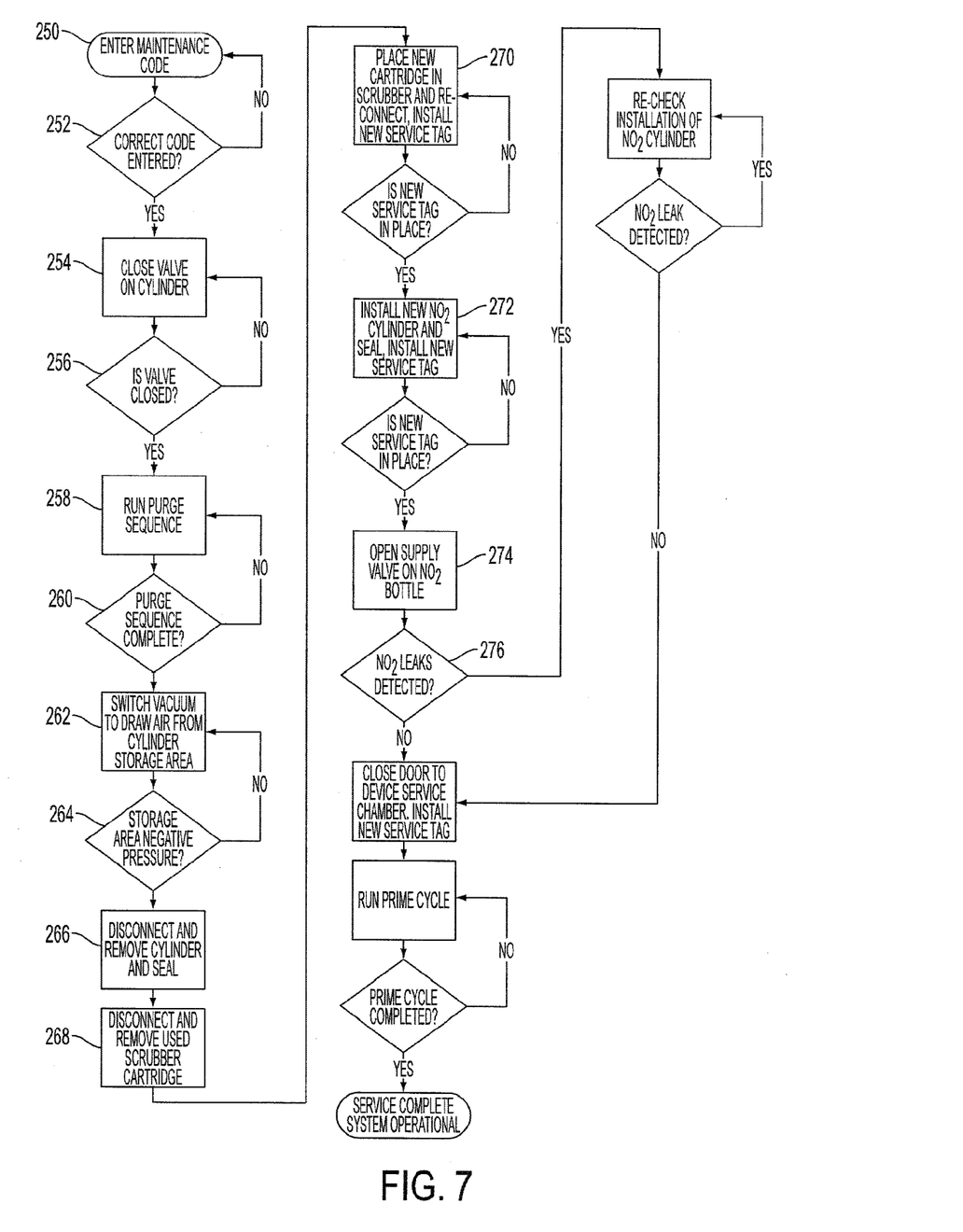
FIG. 7 is a flowchart illustrating a procedure for replacement of consumables in accordance with an embodiment of the present invention.
Figure 8:
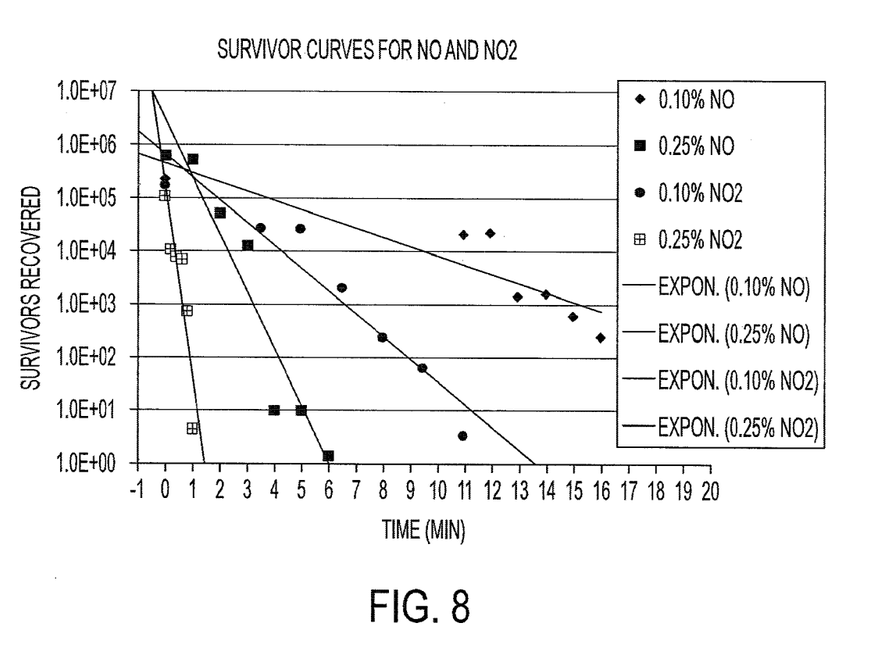
FIGS. 8 and 9 are charts illustrating results using varying concentrations of sterilant gas in accordance with embodiments of the present invention.
Figure 9:
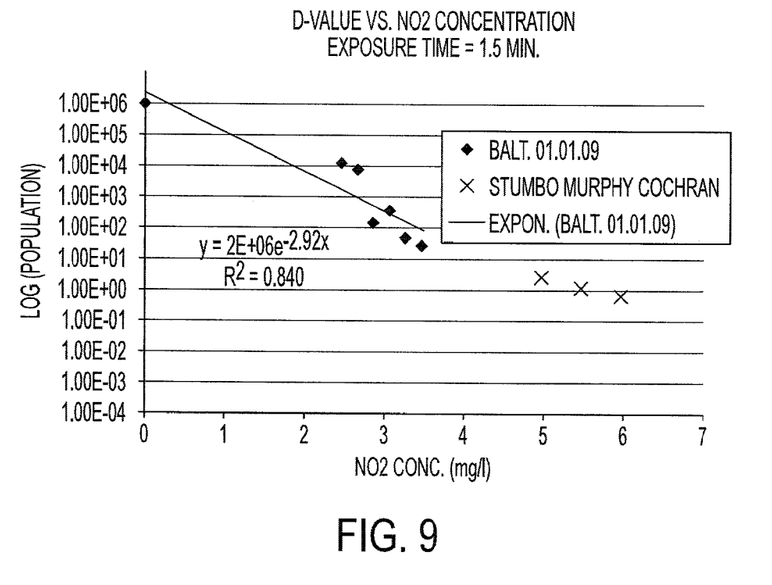

FIG. 7 is a flowchart illustrating an embodiment of a replacement procedure for consumable elements of the device. Inputs and outputs of this procedure may be, for example, displayed on the graphical user interface described above or using other display and input devices.

The procedure begins as a maintenance code is entered 250, and checked 252. In response to the correct code, the cylinder valve is closed 254 and checked 256. Once closed, a purge sequence is run 258. Upon a determination 260 that the purge sequence is complete, a vacuum is activated 262 to draw air from the cylinder storage area. When negative pressure is detected in the storage area 264, the user may disconnect and remove the cylinder and seal 266. The scrubber cartridge may also be removed 268 at this time. The user then installs a new cartridge and corresponding service tag 270 and a new gas cylinder and seal 272. Once installed, the new bottle is opened 274 and a leak check is performed 276. The service door is closed 278 and a new service tag is installed. Note that though this procedure describes replacing both serviceable items at once, they may likewise be replaced independently within the scope of the invention.

Control of the device may be implemented using a graphical user interface. The graphical user interface can include, for example, controls for run parameters (e.g., dosage/concentration of sterilant gas, pressure limits, cycles, dwell times, target pressures, etc.), readouts of metrology devices (e.g., timers, thermometers, pressure transducers, etc.) and controls or status outputs for various of the valves and compressors of the system. System warnings (e.g., interlock warnings) can also be displayed via the graphical user interface. Alternately, the entire process may be automated such that no user input is required and the user interface may simply be replaced by a display or other status indicators.

In an embodiment, in addition to an automated sterilization cycle, the entire process including inserting and removing the object to be sterilized may be automated. In this approach, a robotic handler is provided that can convey the object to be sterilized into the chamber, and remove it upon completion of the sterilization cycle.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of sterilizing an object comprising, in the following order:
   depressurizing a pre-chamber in controllable fluid communication with a liquid nitrogen dioxide supply;
   allowing a controlled dose of nitrogen dioxide from the liquid nitrogen dioxide supply to flow into the pre-chamber;
   isolating the pre-chamber from the liquid nitrogen dioxide supply;
   opening a fluid communication channel between the pre-chamber and a depressurized sterilization chamber containing the object, and
   exposing the object to the nitrogen dioxide in a gaseous state for a selected duration, at a selected pressure and in a selected concentration.

2. A method as in claim 1, further comprising, after opening the fluid communication channel, providing pressurized gas to the pre-chamber, such that the pressurized gas and a portion of an amount of nitrogen dioxide remaining in the pre-chamber flow into the sterilization chamber.

3. A method as in claim 1, wherein the allowing a controlled dose of nitrogen dioxide from the liquid nitrogen dioxide supply to flow into the pre-chamber further comprises:
   measuring a pressure in the pre-chamber; and
   when the measured pressure reaches a threshold selected to provide a dose selected to achieve the selected concentration, isolating the pre-chamber from the liquid nitrogen dioxide supply.

4. A method as in claim 3, further comprising measuring a temperature of the pre-chamber and wherein the threshold is adjusted based on the measured temperature.

5. A method as in claim 1, wherein the concentration of nitrogen dioxide gas is between about 5 mg/L and about 15 mg/L.

6. A method as in claim 1, wherein the exposing further comprises:
   exposing the object a first time to the nitrogen dioxide for a first selected duration, at a first selected pressure and in a first selected concentration;
   after the first exposing, removing the nitrogen dioxide from the sterilization chamber; and
   exposing the object a second time to the nitrogen dioxide for a second selected duration, at a second selected pressure and in a second selected concentration.

7. A method as in claim 6, wherein the first selected time, pressure and concentration are the same as the second selected time, pressure and concentration.

8. A method as in claim 6, wherein the removing comprises evacuating the sterilization chamber into a co-chamber and the exposing a second time comprises allowing contents of the co-chamber to flow into the sterilization chamber.

9. A method as in claim 8, wherein, the exposing a second time comprises adding humidity to the chamber to replace humidity lost to condensation during the removing.

* * * * *